United States Patent [19]

Weil

[11] Patent Number: 5,073,112

[45] Date of Patent: Dec. 17, 1991

[54] ACTIVE/PASSIVE DENTAL POSTS

[75] Inventor: Eberhard Weil, Friedberg, Fed. Rep. of Germany

[73] Assignee: Coltene/Whaledent, New York, N.Y.

[21] Appl. No.: 611,177

[22] Filed: Nov. 8, 1990

[51] Int. Cl.⁵ .................................................. A61C 5/08
[52] U.S. Cl. .................................... 433/221; 433/220; 433/224
[58] Field of Search ............... 433/220, 221, 219, 225, 433/224

[56] References Cited

U.S. PATENT DOCUMENTS

| | | | |
|---|---|---|---|
| 965,246 | 7/1910 | Stallman | 433/221 |
| 1,517,500 | 12/1924 | Fredericks | 433/221 |
| 2,536,669 | 1/1951 | Thau-Jensen | 433/221 |
| 4,515,565 | 5/1985 | Winter-Moore et al. | 433/221 |
| 4,622,012 | 11/1986 | Smoler | 433/221 |
| 4,778,388 | 10/1988 | Yuda et al. | 433/221 |

FOREIGN PATENT DOCUMENTS

| | | | |
|---|---|---|---|
| 662939 | 11/1987 | Czechoslovakia | 433/225 |
| 275 | 5/1979 | World Int. Prop. O. | 433/221 |

Primary Examiner—John J. Wilson
Assistant Examiner—Michael Lynch
Attorney, Agent, or Firm—Helfgott & Karas

[57] ABSTRACT

A dental post for securely retaining a dental restoration in a prepared tooth stub. The dental post is formed of an elongated cylindrical rod having an active threaded portion and a passive portion. The dental post is threadedly engaged with a sleeve secured in the tooth stub, which sleeve has at least an active threaded portion.

20 Claims, 3 Drawing Sheets

ACTIVE/PASSIVE DENTAL POSTS

BACKGROUND OF THE INVENTION

This invention relates to dental posts, and more particularly to a dental post with an active upper portion and a passive lower portion, which improves its retention within a prepared tooth stub on which a dental restoration will be erected. In addition, this invention relates to the use of a sleeve with an active portion positioned in a tooth stub. The active portion of the dental post is engaged with the active portion of the sleeve to improve its retention within the prepared tooth stub. Furthermore, this invention contemplates forming the sleeve by positioning a mandrel with an active upper portion in an adhesive prepared bore in a tooth stub and curing the adhesive to form the sleeve. In one embodiment the adhesive is cured by transmitting light through the mandrel to cure the adhesive.

In restoring dentition, one procedure is to build up a dental prosthetic structure on a tooth stub. The tooth stub is initially prepared by cutting it down to provide a suitable support on which the prosthetic structure will be built. A bore is formed into the tooth stub in which a dental post is inserted. In one type of dental post, referred to as an active post, there are threads provided on the post and the post is threaded into the bore in the tooth stub. Other posts are referred to as passive posts and they are secured in the bore by means of cement. The passive posts typically include a contoured surface for improving its retention in the bore formed in the tooth stub. Suitable dental cement is used for retaining the dental post in the bore. A portion of the dental post extends upwardly above the surface of the tooth stub so that as the dental prosthetic structure is formed or built up onto the tooth stub, it is retained in place on the tooth stub by means of the extending portion of the dental post.

By way of example, an early type of active post has been suggested in U.S. Pat. No. 702,111 describing a post with screw threads which are screwed into the root cavity of a tooth. Threaded engagement of an active post into the dentin of a tooth has been found to cause stress in the tooth thereby contributing to its possible fracture. On the other hand, using passive posts produce less stress in the tooth. However, the retention of passive posts are not as great as the active post. To improve the retention, various types of contoured surfaces have been suggested. By way of example, U.S. Pat. No. 4,479,783, issued Oct. 30, 1984 for "Helically Fluted Dental Post", assigned to the assignee of the present invention, suggests contouring the surface of a passive dental post with helical flutes in a sequence with designated flutes being deeper than alternating shallow flutes to improve retention of the dental post. Improvements in the capabilities of dental posts are also described in U.S. Pat. No. 4,729,736, issued Mar. 8, 1988 for "Contoured Dental Posts", assigned to the assignee of the present invention, which includes helical grooves and annular retaining ledges axially spaced along the post to both improve retention of the post and increase the strength of the post to reduce the possibility of post shear.

The us of sleeves in a prepared bore of a tooth stub has been suggested in the prior art related to retention of a dental post within a bore in a tooth stub. By way of example, there has been suggested in U.S. Pat. No. 965,246 the use of a sleeve in a cavity in a tooth stub into which a pin attached to a crown is inserted and held either by friction or cement. In addition, U.S. Pat. No. 4,622,012 suggests the use of a sleeve positioned in a bore of a tooth through which an adhesive is introduced into the bore. A dental post is then introduced into the sleeve to force the adhesive through holes in the sleeve to distribute the adhesive in the bore. Upon hardening of the adhesive, the post is retained in the sleeve.

While the aforementioned dental posts and sleeves have provided improvements with respect to the retention of a post in a bore, still further improvements in such retention would be beneficial. These improvements would be particularly beneficial if they can be achieved without increasing the risk of breaking the dental post or adding stress to the tooth.

SUMMARY OF THE INVENTION

Accordingly, it is an object of the present invention to provide an improved dental post.

A further object of the present invention is to provide a dental post having improved retention capabilities when secured in a prepared bore in a tooth stub.

Still a further object of the present invention is to provide a dental post with a threaded active portion and either a smooth or contoured passive portion for securing the post to the tooth.

Another object of the present invention is to provide a dental post which is secured to a tooth by engaging a sleeve positioned in a prepared bore in the tooth stub.

Still another objective of the present invention is to secure a dental post having an active portion and a passive portion by providing a sleeve in a prepared tooth cavity when engages the active portion of the post.

Still another object of the present invention is to secure in a tooth stub an improved dental post having an active portion and a passive portion by inserting the active and passive post portions of the post within active and passive portions of a sleeve, respectively, which sleeve is formed in a prepared bore in a tooth stub.

Yet a further object of the present invention is to provide a sleeve in a prepared bore in a tooth, which sleeve is complementary to a dental post having an active portion and a passive portion.

Another object of the present invention is to form a sleeve in a prepared bore in a tooth by surrounding a mandrel positioned in the prepared bore in the tooth stub with a curable adhesive and curing the adhesive in the tooth stub to form the sleeve.

Another object of the present invention is to form a sleeve in a prepared bore in a tooth by transmitting light through a mandrel to cure a material which when cured forms the sleeve.

Still another objective of the present invention is to provide a dental post with an active portion and a passive portion within a cement prepared sleeve which in turn is formed in a prepared bore of a tooth stub, thereby improving the retention of the post in the tooth stub.

Briefly, in accordance with the present invention there is provided a dental post for securely retaining a dental restoration on a prepared tooth stub. The dental post includes an elongated cylindrical rod having an elongated longitudinal axis. The rod has an upper active portion with threads formed in the periphery of the rod and a lower passive portion which may be contoured.

The active and passive portions of the rod retain the rod within a prepared bore in a tooth stub.

In one embodiment of the invention a sleeve is provided in a bore of a tooth with the sleeve having an upper portion with threads complementary to the threads in the active upper portion of the rod. The threaded engagement of the active portions of the rod and sleeve improve the retention of the rod in the tooth stub without causing stress on the tooth.

In addition, the present invention contemplates providing the sleeve by positioning a mandrel having a threaded upper portion of the same size and shape as the active upper portion of the rod of the dental post, in a prepared bore of a tooth stub and introducing an adhesive into the bore which when it hardens, forms the sleeve. The mandrel is withdrawn from the sleeve leaving a threaded upper portion for the threaded portion of the rod to engage.

In another embodiment of the invention the mandrel is made of a light transmitting material and the adhesive which forms the sleeve is made from a light curable material. Light is transmitted by the mandrel to the light curable material which hardens and adheres to the bore in the tooth stub to form the sleeve.

The aforementioned objects, features and advantages of the invention, will, in part, be pointed out with particularity, and will, in part, become obvious from the following more detailed description of the invention taken, in part, with the drawings which form an integral part thereof.

BRIEF DESCRIPTION OF THE DRAWINGS

In the drawings.

In the various figures of the drawings like reference characters designate like parts.

DETAILED DESCRIPTION OF THE PREFERRED EMBODIMENT

Figure 1:
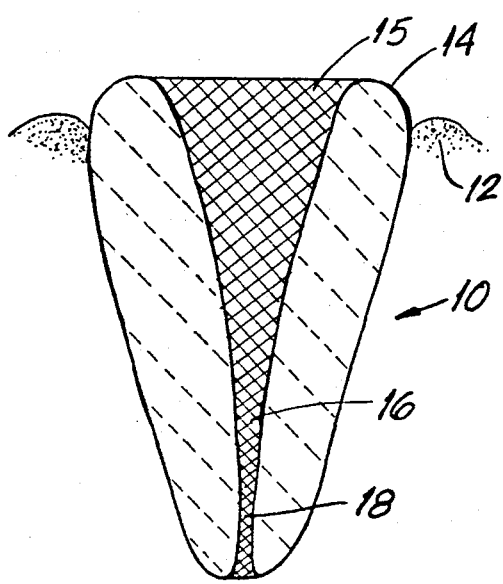
FIG. 1 is a cross sectional view taken through a tooth stub showing the normal preparation of an endodontically treated tooth stub ready for utilization of the dental post of the present invention.

Referring now to the drawings, in FIG. 1 there is shown a tooth stub 10 in cross section within a gum area 12, where the upper end of the tooth has been impaired. The tooth has been initially cut down, typically to provide a suitable upper surface 14 to support a dental restoration. In order to build up a dental restoration or other super structure onto the tooth stub 10, there is required a retaining member, such as the dental post of the present invention.

Figure 2:
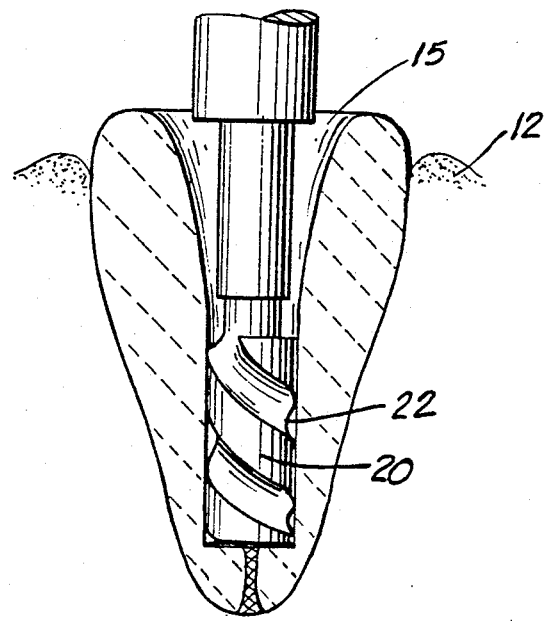
FIG. 2 is another view of the tooth stub shown in FIG. 1, being sized to prepare the canal in the tooth stub for the post.

Initially, conventional root canal work is carried out by cleaning out the canal 15 of the tooth along the canal section 16 of a tooth stub. The canal is sealed with a suitable sealant 18 such as gutta percha. As shown in FIG. 2 a twist drill 20 is used to remove gutta percha and to size the canal to the desired bore 22 in the canal section 16 of the tooth stub.

Figure 5:
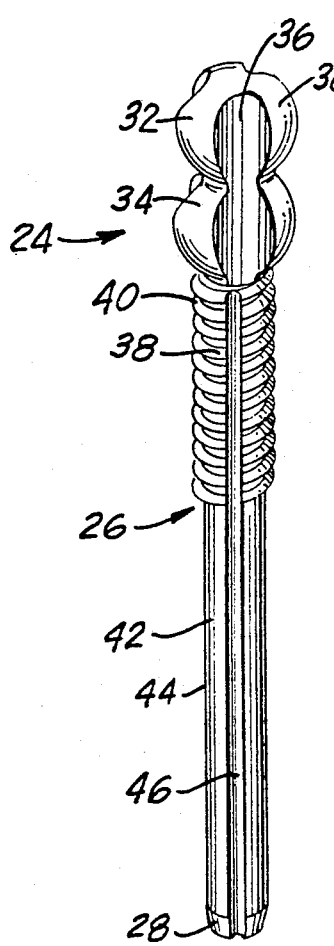
FIG. 5 is a perspective view of a dental post having an active upper portion and a passive lower portion in accordance with the present invention.

Referring to FIG. 5, the dental post of the present invention is shown generally at 24 and comprises an elongated cylindrical rod 26 having an enlarged longitudinal axis and a substantially flat lower end 28 and a head 30 at its upper end. The head 30 includes a pair of spheres 32, 34 with elongated indentations 36 triangularly positioned about the spheres.

The upper portion 38 of the shaft 26 has threads 40 formed in the periphery of the rod. Since, as will be described later, the threaded upper portion positively engages threads in a sleeve, the threaded portion is also referred to as an active portion. The lower portion 42 of rod 26 has a smooth outer surface 44 and an elongated vertical channel 46 which serves as a vent during insertion of the post 24 into a tooth stub. Since the lower portion 42 is not threaded, it serves as a passive portion.

Figure 6:
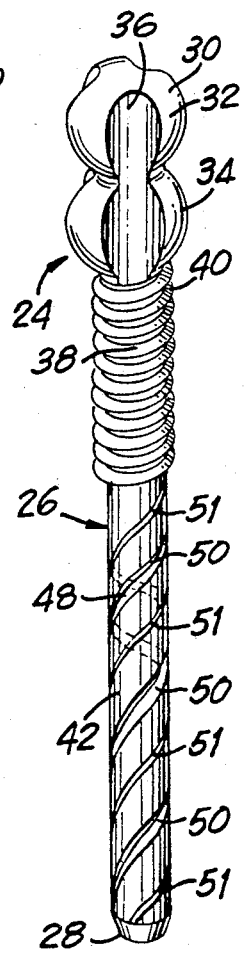
FIG. 6 is a perspective view of another embodiment of a dental post having an upper active portion and a passive lower portion in accordance with the present invention.

FIG. 6 depicts another post 24 of the present invention wherein the lower passive portion 42 of the rod 26 is provided with multiple helical grooves 48 which wind about the periphery of the pin. These grooves are typically flutes of the type described in the aforementioned U.S. Pat. No. 4,479,783. As therein described, certain of the flutes are deeper flutes 50 and are interspersed with shallower flutes 51. As a result of the multiple flute lines which terminate at the lower end 28, the flute lines serve as a vent during insertion of the post 24 into a tooth stub.

Figure 7:
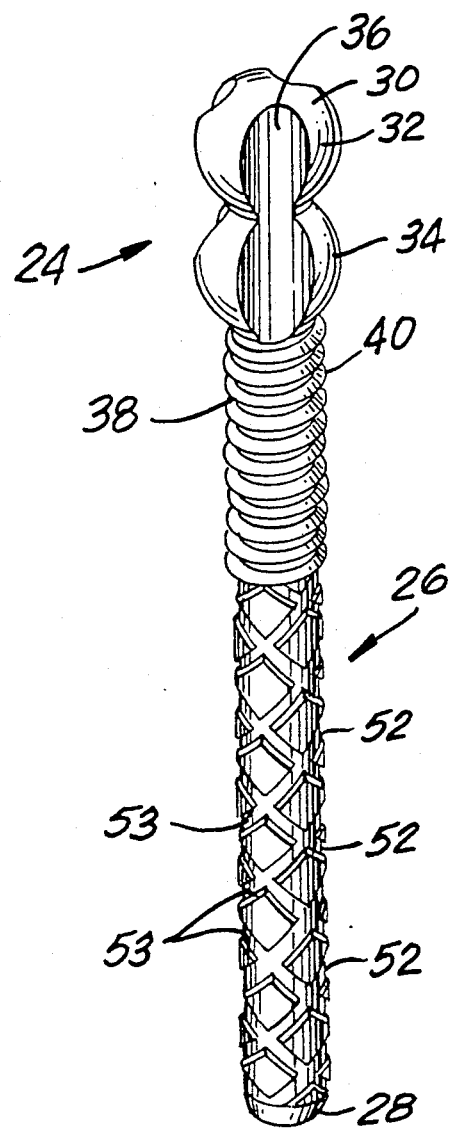
FIG. 7 is a perspective view of another embodiment of a dental post having an upper active portion and a passive lower portion in accordance with the present invention.

FIG. 7 depicts another post 24 of the present invention wherein the lower passive portion 42 of the rod 26 is provided with multiple helical grooves 52 and 53 which wind about the periphery of the pin. Grooves 52 and grooves 53 wind in opposite directions about the pin and intersect to form a diamond-shaped pattern. As a result of the multiple grooves which terminate at the lower end 28, the grooves serve as a vent during insertion of the post 24 into a tooth stub.

Numerous other configurations of the passive portion 42 of the present invention are within the contemplation of the present invention. For example, the configuration described in aforementioned U.S. Pat. No. 4,729,736 which includes helical grooves and annular retaining ledges could be used.

Figure 3:
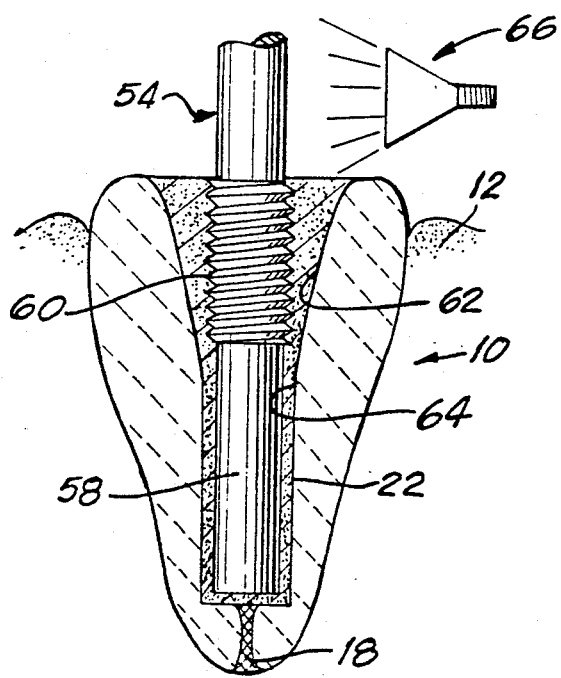
FIG. 3 is a cross sectional view of a drilled tooth stub with a prepared canal, showing a light transmitting mandrel positioned in the canal and surrounded by an adhesive.

Referring next to FIG. 3, there is shown a mandrel 54 having an upper portion 56 and a lower portion 58. The mandrel 54 is cylindrical with an elongated longitudinal axis and has threads 60 formed in the periphery of the upper portion 56. The threads 60 have substantially the same pitch and diameter as threads 40 formed in the upper portion 38 of cylindrical rod 26. The upper threaded portion of the mandrel 56 is also referred to as the active portion of the mandrel. The lower portion 5 of the mandrel is smooth and is also referred to as the passive portion of the mandrel.

In accordance with the present invention, mandrel 54 is placed with its passive portion 58 inserted in enlarged bore 22 of the tooth stub 10. A sleeve or liner 62 is cast by filling the space between the mandrel 54 and the inner surface 64 of the tooth with an adhesive which will cure and harden in the manner of forming a cast. The adhesive may be any one of the many dental adhesives used to attach a dental post to a tooth stub, e.g., a self curing adhesive.

In the preferred embodiment of the invention, the mandrel 54 is made of a light transmitting medium and acts as a light pipe. The adhesive is a light-curable composite which will begin to cure when light is transmitted to its surface. Light from a light source 66 is shined on mandrel 54 which transmits the light to the composite to cause curing. The mandrel 54 is also made of a material which will not form a strong bond with the composite. Alternatively, mandrel 54 can be coated with a compound which will prevent it from forming a strong bond with the composite. Alternately, the adhesive can be a self-curing composite and it will set by itself in adequate time.

After the composite has hardened, mandrel 54 is unscrewed from the cured composite leaving cast sleeve 62 (FIG. 4) bonded to the inner surface 64 of tooth stub 10. Although not necessary to the success of the present invention, mandrel 54 is preferably placed coaxially in bore 22 to form a sleeve 62 of fairly uniform dimensions.

Figure 4:
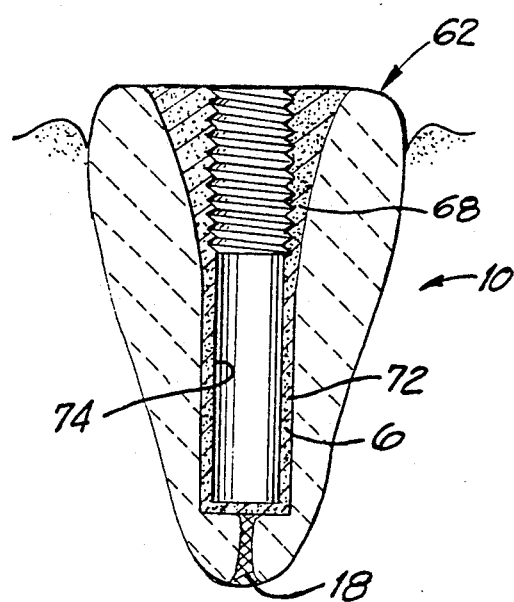
FIG. 4 is another cross sectional view of the tooth stub shown in FIG. 3 with the mandrel removed leaving a preformed sleeve in the bore of the tooth stub.

As shown in FIG. 4, sleeve 62 with mandrel 54 removed has an upper portion 68 with threads 70 formed by the threads 60 of the mandrel. Sleeve 62 has a lower portion 72 with a smooth inner surface 74. The threaded upper portion of the sleeve is also referred to as the active portion of the sleeve. The smooth lower portion of the sleeve is also referred to as the passive portion of the sleeve.

Dental post 24 having either a smooth or a contoured lower portion 42 will threadedly engage sleeve 62 since the pitch and diameter of the threads 40 of the post 24 are the same as those of the threads 60 used to form threads 70 in the sleeve. Consequently, dental post 24 is secured to tooth 10 by inserting rod 26 into sleeve 62 and threading the active portion 38 of the rod into the active portion 56 of the sleeve.

Figure 9:
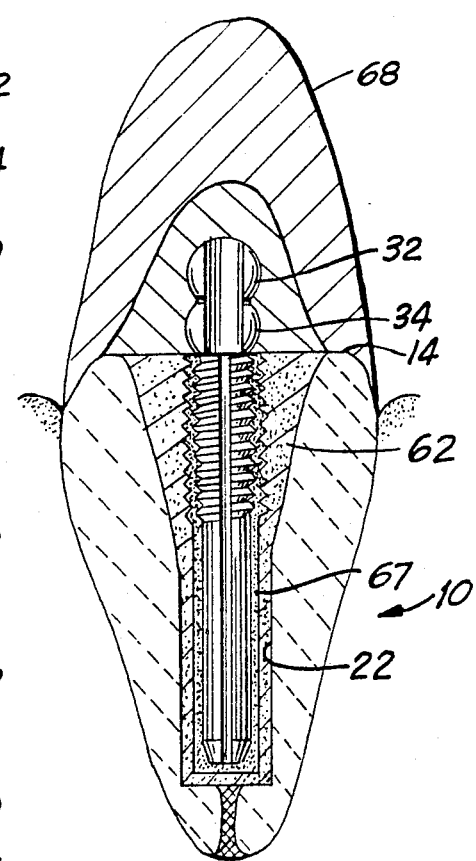
FIG. 9 is a cross sectional view of a tooth stub and dental restoration, showing the use of the present invention for securing the dental restoration on the tooth stub.
Figure 8:
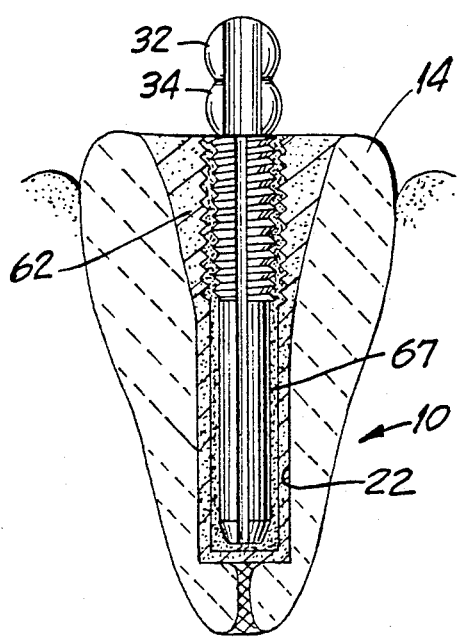
FIG. 8 is a cross sectional view of a tooth stub, showing a dental post in accordance with the present invention retained within the stub.

In one embodiment of the invention shown in FIGS. 8 and 9, dental post 24 is threadedly engaged with sleeve 62. In addition, the sleeve 62 has been prepared with a dental cement 67 which will bond both the active and passive portions of the post to the active and passive portions of the sleeve. The use of the cement gives even further improved retention of the post in the tooth stub.

Head 30 of post 24 extends upwardly above the upper surface 14 of tooth stub 10. A superstructure 68a can then be suitably formed onto the tooth stub in accordance with standard well known techniques in the dental line. The superstructure 68a is retained onto the mating spheres 32, 34 and is held securely in place.

Figure 10:
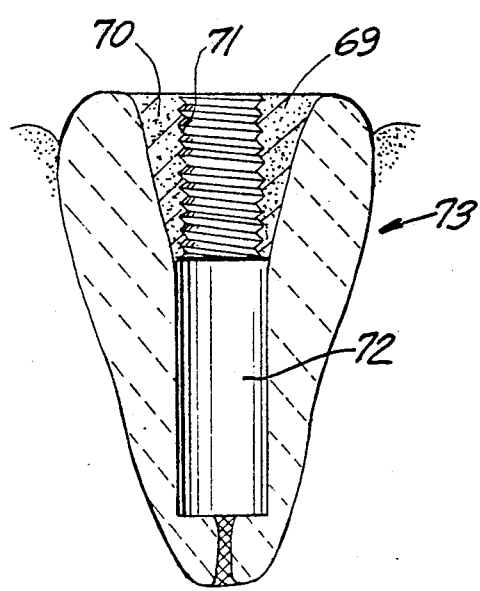
FIG. 10 is a cross sectional view of a tooth stub, showing a sleeve having a threaded active portion in the upper part of the stub.

An alternate embodiment is shown in FIG. 10 in which a sleeve 69 has only an active portion 70 with threads 71. One way of forming sleeve 69 is to use a mandrel (not shown) with a passive portion having an outer diameter equal to the inner diameter of a prepared bore 72 in a tooth stub 73. When the mandrel is positioned in bore 72 of tooth stub 73, a curable adhesive is introduced around the active portion of the mandrel. The adhesive will not enter the bore 72 since the tight fit of the passive portion of the mandrel in the bore prevents the adhesive from flowing into the bore. When the adhesive has cured, the mandrel is removed leaving a sleeve 69 with only an active portion 70.

Dental post 24 is positioned in tooth stub 73 with the passive portion 42 in bore 72 and active portion 38 threadedly engaged with threads 71 of sleeve 69. A dental cement is used between dental post 24 and sleeve 69. Cement is introduced into bore 72 to increase retention of post 24 by bonding the passive portion 42 of post 24 within the tooth stub.

It should be noted that the use of cement to increase the retention of the post 24 in a tooth stub, requires that the dimensions of the post and the sleeve be selected so that the cement will not interfere with placing the post in the tooth stub, i.e. there must be sufficient clearance between the post and the sleeve.

There has been described a preferred and alternate embodiments of the invention. However, it should be understood that various changes and modifications may be made thereto without departing from the spirit and scope of the invention.

What is claimed is:

1. A dental post assembly for securely retaining a dental restoration on a prepared tooth stub in which the tooth stub has an enlarged bore in the canal section of the tooth stub, comprising:

a sleeve made of curable hardened adhesive and securable to a surface of said canal section, said sleeve being formed by positioning a mandrel having an active threaded portion and a passive portion in the tooth stub with the passive portion of the mandrel in the bore of the tooth stub, wherein at least the active portion of the mandrel is surrounded with said curable adhesive which hardens to form said sleeve, said sleeve having an outer peripheral wall which is in direct contact with and secured to the surface of the canal section when said sleeve is formed, said sleeve having a closed bottom wall and including an active threaded portion and a passive portion; and an elongated rod having an active threaded portion and a passive portion, said active portion of said rod having threads of a pitch and diameter corresponding to a pitch and diameter of threads of said active threaded portion of said sleeve to permit the rod to be threadedly and removably engaged with the sleeve.

2. A dental post assembly as in claim 1, wherein said active portion and passive portion of said sleeve are formed by hardening said curable adhesive which surrounds the mandrel.

3. A dental post assembly as in claim 1, wherein a dental cement is provided between the rod and the sleeve.

4. A dental post assembly as in claim 1, wherein the mandrel is made of a light transmitting medium and the curable adhesive is cured by exposure to light.

5. A dental post assembly as in claim 1, wherein said adhesive is made of a self curing adhesive material.

6. A dental post assembly as in claim 1, wherein said passive portion of the rod is contoured.

7. A dental post assembly for securely retaining a dental restoration on a prepared tooth stub in which the tooth stub has an enlarged bore in the canal section of the tooth stub, comprising:

a sleeve formed of a non-metallic material securable in said tooth stub, said sleeve having a closed bottom wall and including an active threaded portion on an inner surface thereof and a non-threaded passive portion; and an elongated cylindrical rod insertable in said sleeve and having an active threaded portion and a non-thread passive portion, said active threaded portion of said rod being threadedly and removably engaged within said active threaded portion of the sleeve to retain the rod in the tooth stub, said sleeve having an outer peripheral surface which is in direct contact with and secured to a wall surface of said bore when said sleeve is secured in said tooth stub.

8. A dental post assembly as in claim 7, wherein the passive portion of the sleeve is positioned in the tooth stub, and the passive portion of the cylindrical rod is positioned within the passive portion of the sleeve.

9. A dental post assembly as in claim 7, wherein a dental cement is provided between the rod and the sleeve.

10. A dental post assembly as in claim 7, wherein said non-metallic material is hardened curable adhesive.

11. A dental post assembly for securely retaining a dental restoration on a prepared tooth stub in which the tooth stub has an enlarged bore in the canal section of the tooth stub, comprising:

a sleeve formed of curable hardened adhesive and adapted to be secured in said bore, said sleeve having a closed bottom wall and including an active threaded portion and a passive portion; and an elongated rod having an active threaded portion and a passive portion, wherein said active portion of said rod has threads of a pitch and diameter corresponding to a pitch and diameter of threads of said active threaded portion of said sleeve which permit the rod to be threadedly and removably engaged with the sleeve, said sleeve having an outer peripheral surface which is in direct contact with a wall of said bore when said sleeve is secured in said bore.

12. A dental post assembly as in claim 11, wherein said passive portion of said sleeve surrounds the passive portion of the rod.

13. A dental post assembly as in claim 11, wherein a dental cement is provided between the rod and the sleeve.

14. A dental post assembly as in claim 11, wherein said adhesive is made of a self curing adhesive material.

15. A method of providing a dental post assembly for securely retaining a dental restoration on a prepared tooth stub which has an enlarged bore in a canal section of the tooth stub, the method comprising the steps of:

positioning a mandrel having an active threaded upper portion and a passive portion in the tooth stub with the passive portion of the mandrel in the bore of the tooth stub;

surrounding at least the active portion of said mandrel while a curable adhesive which hardens to form a sleeve having an active portion and a passive portion which becomes secured to a surface of said canal as the adhesive hardens;

providing a dental post formed by an elongated rod having an active threaded portion and a passive portion wherein said active portion has threads of a pitch and diameter which permits the tooth to be threadedly engaged with the sleeve;

removing said mandrel from said sleeve; and positioning said dental post in said sleeve whereby said active threaded portion of said elongated rod threadedly engages in said sleeve.

16. A method as in claim 15, further including a step of providing a dental cement between said rod and said sleeve.

17. A method as in claim 15, wherein said mandrel is made of a light transmitting medium and the curable adhesive is cured by exposure to light.

18. A method as in claim 15, wherein said adhesive is made of a self-curing adhesive material.

19. A method as in claim 15, wherein said mandrel is made of a material preventing a strong bond between said mandrel and said adhesive.

20. A method as in claim 15, wherein said mandrel is provided with a coating preventing a strong bond between said mandrel and said adhesive.

* * * * *